United States Patent [19]

Tanabe et al.

[11] 4,319,110

[45] Mar. 9, 1982

[54] MICROWAVE OVEN EMPLOYING A GAS SENSOR

[75] Inventors: Takeshi Tanabe, Higashiosaka; Hideshi Nakagawa, Osaka; Takeshi Fujihara, Nara, all of Japan

[73] Assignee: Sharp Kabushiki Kaisha, Osaka, Japan

[21] Appl. No.: 152,421

[22] Filed: May 22, 1980

[30] Foreign Application Priority Data

May 22, 1979 [JP] Japan .................................. 54-64681

[51] Int. Cl.³ .............................................. H05B 6/68
[52] U.S. Cl. .............................................. 219/10.55 B
[58] Field of Search .................. 219/10.55 B, 10.55 R, 219/10.55 M; 73/421 R

[56] References Cited

U.S. PATENT DOCUMENTS 4,162,381 7/1979 Buck ............................. 219/10.55 B Primary Examiner—Arthur T. Grimley
Attorney, Agent, or Firm—Birch, Stewart, Kolasch and Birch

[57] ABSTRACT

A microwave oven includes a gas sensor for detecting the concentration of gas developed from a foodstuff disposed in an oven cavity. When the cooking operation is conducted to a desired level, the gas concentration reaches a preselected level and, hence, an output signal of the gas sensor shows a predetermined output level at which the microwave generation is terminated. An abnormal condition detection circuit is provided for detecting an abnormally high resistance created in the gas sensor due to, for example, disconnection of a warming heater included in the gas sensor. When an abnormal condition is detected by the abnormal condition detection circuit, the microwave generation is terminated and an alarm display is conducted to inform the operator of the abnormal condition.

5 Claims, 5 Drawing Figures

MICROWAVE OVEN EMPLOYING A GAS SENSOR

BACKGROUND AND SUMMARY OF THE INVENTION

The present invention relates to a microwave oven and, more particularly, to a microwave oven including a control circuit responsive to an output signal derived from a gas sensor disposed in an exhaustion gas path of the microwave oven.

Recently, a gas sensor output controlled microwave oven has been developed, wherein the microwave generation is terminated when a gas sensor output reaches a preselected level. A typical control circuit is described in copending application, "COOKING UTENSIL CONTROLLED BY GAS SENSOR OUTPUT", Ser. No. 71,179, filed on Aug. 31, 1979 by Takeshi Tanabe and assigned to the same assignee as the present application.

In such a gas sensor output controlled microwave oven, a stable operation of the gas sensor is strictly required to ensure a stable operation of the microwave cooking. However, there is a possibility that a warming heater included in the gas sensor is disconnected while the microwave cooking operation is performed.

Accordingly, an object of the present invention is to provide a gas sensor output controlled microwave oven of a stable operation.

Another object of the present invention is to provide a detection system for detecting an abnormal condition of a gas sensor included in a microwave oven.

Still another object of the present invention is to provide a control circuit for automatically terminating the microwave generation when an abnormal condition is detected in a gas sensor included in a microwave oven.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a level detection system is provided for detecting an abnormal level of an output signal derived from a gas sensor disposed in a microwave oven. When an abnormal output level of the gas sensor is detected, the microwave generation is automatically terminated and an alarm display is achieved.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
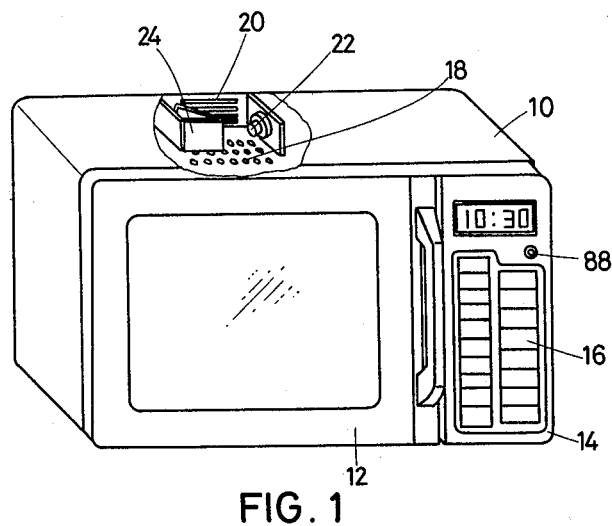
FIG. 1 is a partially cut-away perspective view of an embodiment of a microwave oven of the present invention.

A microwave oven of the present invention mainly comprises a casing 10, an oven door 12, and a control panel 14 on which a plurality of key switches 16 are disposed for introducing a desired command into the microwave oven. The microwave oven further includes an oven wall for defining an oven cavity, and a magnetron disposed in the clearance formed between the casing 10 and the oven wall for supplying the microwave energy into the oven cavity. A blower fan system is provided for introducing a fresh air into the casing 10, cooling the magnetron, and introducing the air into the oven cavity for recirculation purposes while the microwave cooking is performed.

An exhaustion path is provided between the oven wall and the casing 10. More specifically, openings 18 are formed in the upper wall of the oven cavity, and an exhaustion outlet 20 is formed in the rear wall of the casing 10. An exhaustion gas developed from the foodstuff disposed in the oven cavity is exhausted through the exhaustion path due to the forced air flow created by the blower fan system. A gas sensor 22 is disposed in the exhaustion path for detecting the concentration of the gas exhausted from the oven cavity. A guide plate 24 is disposed in the exhaustion path for directing the exhaustion gas toward the gas sensor 22 in order to ensure a stable detection.

Figure 2:
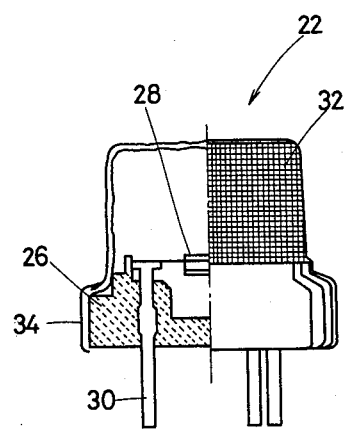
FIG. 2 is a partially sectional front view of a gas sensor included in the microwave oven of FIG. 1.

FIG. 2 shows the gas sensor 22 in detail.

The gas sensor 22 mainly comprises a base member 26 for supporting a sensor element 28, and lead pins 30 for connecting the sensor element 28 to the control circuit of the microwave oven. A gauze 32 is secured to the base member 26 through the use of a coupling ring 34 for protecting the sensor element 28 but for exposing the sensor element 28 to the exhaustion gas.

Figure 3:
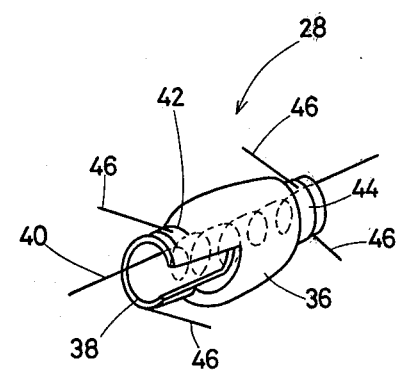
FIG. 3 is a perspective view of a sensor element included in the gas sensor of FIG. 2.

The sensor element 28 mainly comprises, as shown in FIG. 3, a $SnO_2$ sintered block 36 secured around a ceramic pipe 38, and a warming heater 40 disposed through the ceramic pipe 38 for warming the $SnO_2$ sintered block 36 for ensuring the stable detection operation. Electrode terminals 42 and 44 are secured to the both ends of the $SnO_2$ sintered block 36. Lead wires 46 are connected to the electrode terminals 42 and 44, and the other ends of the lead wires 46 are connected to the lead pins 30, respectively.

The resistance value of the sensor element 28 decreases as the gas concentration increases. The variation of the sensor element resistance is converted into a voltage level variation for providing a sensor output signal.

Figure 4:
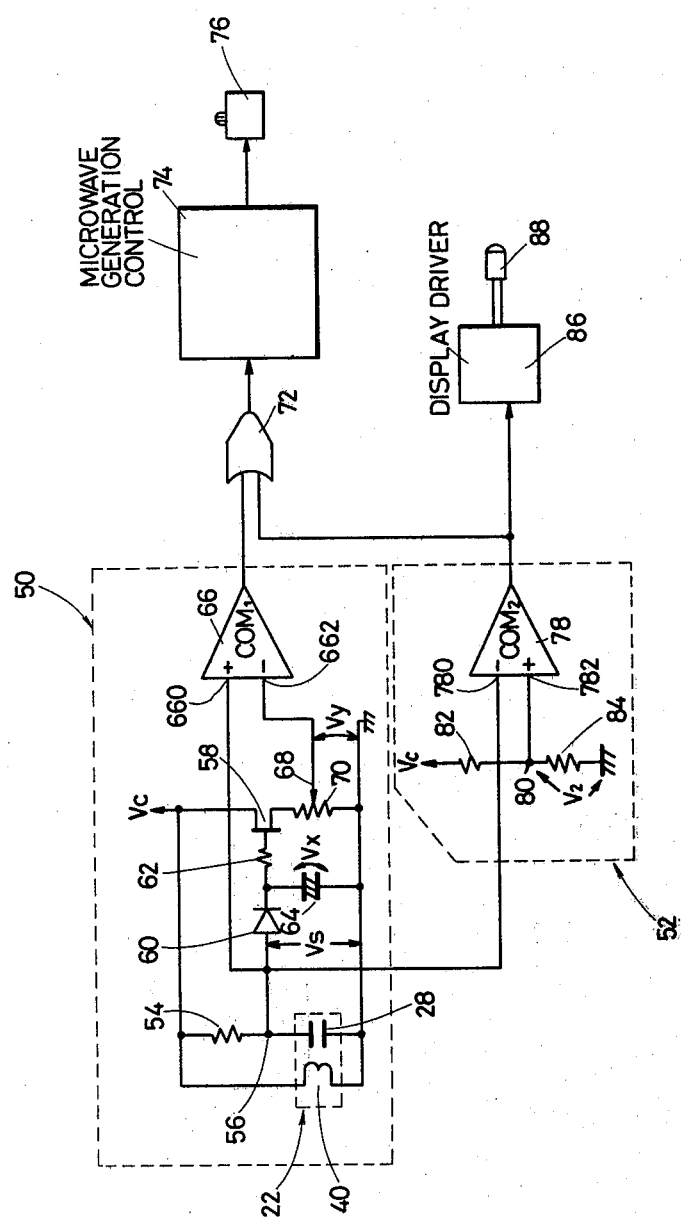
FIG. 4 is a circuit diagram of a control circuit included in the microwave oven of FIG. 1.

FIG. 4 shows an embodiment of a control circuit included in the microwave oven of FIG. 1.

The control circuit mainly comprises a cooking condition detection unit 50 and an abnormal condition detection unit 52. The sensor element 28 is connected to a power supply terminal $V_c$ via a resistor 54. A node 56 provided between the sensor element 28 and the resistor 54 functions as an output terminal of a voltage signal $V_s$. The node 56 is connected to a gate electrode of a field effect transistor 58 through a diode 60 and a resistor 62. A capacitor 64 is connected between the ground terminal and a node provided between the diode 60 and the resistor 62. The capacitor 64 functions to memorize the initial maximum output level $V_x$ of the voltage signal $V_s$ derived from the gas sensor 22.

A first comparator 66 is included in the cooking condition detection unit 50. A data input terminal 660 of the first comparator 66 is connected to the node 56 in order to receive the voltage signal $V_s$. A reference signal input terminal 662 of the first comparator 66 is connected to an output terminal 68 of a variable resistor 70. The variable resistor 70 is interposed within the source-drain path of the field effect transistor 58. The output terminal 68 develops a reference voltage level $V_y$, which is determined by the initial maximum output level $V_x$ of the voltage signal $V_s$ and the division ratio determined by the variable resistor 70. By properly selecting the division ratio of the variable resistor 70 in accordance with the kind of foodstuff to be cooked, a preferred reference voltage level $V_y$ is applied to the reference signal input terminal 662 of the first comparator 66.

In the above constructed cooking condition detection unit 50, the voltage signal $V_s$ can be expressed as follows:

$$V_s = V_c \times R_s/(R_s + R_L)$$

where:

$V_c$ is the power supply level;

$R_s$ is the resistance value of the sensor element 28; and $R_L$ is the resistance value of the resistor 54.

As already discussed above, the resistance value $R_s$ of the sensor element 28 reduces as the gas concentration increases. Therefore, the level of the voltage signal $V_s$ decreases as the concentration of the gas developed from the foodstuff increases. When the voltage signal $V_s$ drops to the reference voltage level $V_y$, the first comparator 66 develops a detection output toward an OR gate 72. The thus obtained detection output is applied to a microwave generation control circuit 74 to terminate the operation of a magnetron 76, thereby completing the microwave cooking operation.

In such a system, if the warming heater 40 is accidentally disconnected, the resistance value $R_s$ of the sensor element 28 becomes abnormally high. More specifically, the normal resistance value of the sensor element 28 is around 10 through 100KΩ. However, the resistance value of the sensor element 28 becomes about 10 MΩ when the warming heater 40 does not operate. Such an abnormally high resistance also occurs when an abnormal condition is created in the sensor element 28. When the sensor element 28 shows the abnormally high resistance, the level of the voltage signal $V_s$ becomes substantially identical with the power supply level $V_c$. It is apparent that the first comparator 66 never develops the detection output when the sensor element 28 shows the abnormally high resistance. In this case, the microwave generation will be continuously performed even though the foodstuff has been cooked to a preferred level.

To prevent the occurrence of the above-mentioned undesirable condition, the control circuit of FIG. 4 includes the abnormal condition detection unit 52. The abnormal condition detection unit 52 mainly comprises a second comparator 78, of which a data input terminal 780 is connected to receive the voltage signal $V_s$ from the node 56, and a reference voltage input terminal 782 is connected to receive a reference voltage $V_2$ from a node 80 which is provided between two resistors 82 and 84. The reference voltage $V_2$ is selected slightly smaller than the power supply level $V_c$.

Accordingly, when the voltage signal $V_s$ becomes abnormally high and reaches the reference level $V_2$, the second comparator 78 develops a detection output. The thus obtained detection output is applied to the microwave generation control circuit 74 through the OR gate 72 for terminating the microwave generation. The detection output derived from the second comparator 78 is also applied to a display driver circuit 86 in order to activate a light emitting diode 88 which is disposed on the control panel 14, thereby informing the operator of the abnormal condition.

Figure 5:
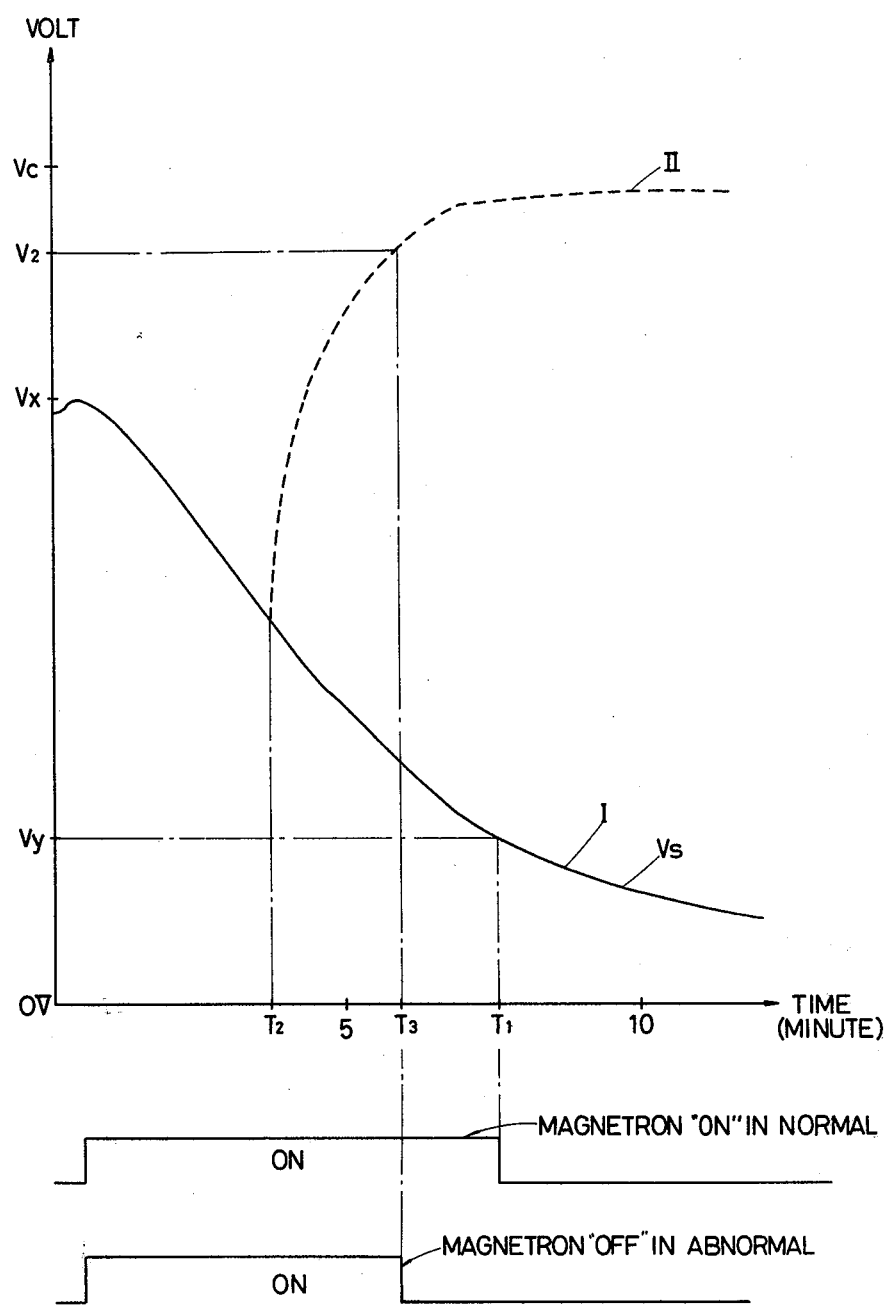
FIG. 5 is a time chart for explaining an operation mode of the control circuit of FIG. 4.

FIG. 5 shows the operational mode of the control circuit of FIG. 4.

A solid curve I represents the normal condition, wherein the microwave cooking operation is controlled by the cooking condition detection unit 50. When the level of the voltage signal $V_s$ is reduced to the preferred reference voltage level $V_y$ determined by the variable resistor 70, the first comparator 66 develops the detection output at a time $T_1$ to terminate the microwave generation. Now assume that the warming heater 40 is disconnected at a time $T_2$. Then, the voltage signal $V_s$ follows a dotted line curve II. When the level of the voltage signal $V_s$ reaches the reference level $V_2$ at a time $T_3$, the second comparator 78 detects the abnormal condition to terminate the microwave generation and activate the alarm display.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A microwave oven comprising:
   a microwave generation source;
   a gas sensor disposed in an exhaustion gas path for detecting the concentration of a gas developed from a foodstuff disposed in an oven cavity;
   microwave generation control means for activating said microwave generation source in accordance with an output signal derived from said gas sensor;
   abnormal condition detection means for detecting an abnormal condition occurring in said gas sensor; and
   control means for precluding the activation of said microwave generation source when a detection output is developed from said abnormal condition detection means.

2. The microwave oven of claim 1, wherein said abnormal condition detection means detects an abnormally high resistance created in said gas sensor.

3. The microwave oven of claim 1, wherein said abnormal condition detection means comprises:
   a comparator having a data input terminal receiving an output voltage signal derived from said gas sensor; and
   a reference voltage applying means for applying a reference voltage signal to a reference input terminal of said comparator.

4. The microwave oven of claim 3, wherein said reference voltage signal has a level substantially identical with the power supply level of said abnormal condition detection means.

5. The microwave oven of claim 1, 2, 3 or 4, further comprising:
   an indicator for alarm display; and
   driver means for activating said indicator when said detection output is developed from said abnormal condition detection means.

* * * * *